(12) United States Patent
Chang et al.

(10) Patent No.: US 8,834,953 B2
(45) Date of Patent: Sep. 16, 2014

(54) METHOD FOR PREPARING NI-CONTAINING MAGNETIC MESOPOROUS SILICA WHOSE SURFACE STRONGLY BINDS HISTIDINE-TAGGED PROTEIN, PROTEIN-BINDING MATERIAL FOR DEGRADING TOXIC AROMATIC COMPOUND COMPRISING THE MAGNETIC MESOPOROUS SILICA, AND METHOD FOR DEGRADING TOXIC AROMATIC COMPOUND USING THE MAGNETIC MESOPOROUS SILICA

(75) Inventors: Jeong Ho Chang, Gwangmyeong-si (KR); Jiho Lee, Seoul (KR); Soo Youn Lee, Gwangmyeong-si (KR)

(73) Assignee: Korea Institute of Ceramic Engineering and Technology, Seoul (KR)

( * ) Notice: Subject to any disclaimer, the term of this patent is extended or adjusted under 35 U.S.C. 154(b) by 339 days.

(21) Appl. No.: 13/208,111

(22) Filed: Aug. 11, 2011

(65) Prior Publication Data

US 2012/0264188 A1    Oct. 18, 2012

(30) Foreign Application Priority Data

Apr. 15, 2011    (KR) .................... 10-2011-0035414

(51) Int. Cl.
*C12N 11/14*    (2006.01)
*B06B 1/20*    (2006.01)
*B05D 3/00*    (2006.01)

(52) U.S. Cl.
USPC ............................ 427/2.1; 427/601; 435/176

(58) Field of Classification Search
None
See application file for complete search history.

(56) References Cited

U.S. PATENT DOCUMENTS 7,868,145 B2 *    1/2011    Wu et al. ................... 530/412
2010/0056360 A1 *    3/2010    Lee .......................... 502/158

OTHER PUBLICATIONS

Tallury et al., 2008. Silica-based multimodal/multifunctional nanoparticles for bioimaging and biosensing applications. Nanomedicine, vol. 3, No. 4, pp. 579-592.*
Kim et al., 2007. Dual-Mode Fluorophore-Doped Nickel Nitrilotriacetic Acid-Modified Silica Nanoparticles Combine Histidine-Tagged Protein Purification with Site-Specific Fluorophore Labeling. Journal of the American Chemical Society, vol. 129, pp. 13254-13264.*
Wang et al. Preparation of magnetic iron/mesoporous silica composite spheres and their use in protein immobilization. Trans. Nonferrous Met. Soc. China 19 (2009) pp. 605-610.*
Yang et al. Magnetite-Containing Spherical Silica Nanoparticles for Biocatalysis and Bioseparations. Anal. Chem 2004. vol. 76, pp. 1316-1321.*

(Continued)

*Primary Examiner* — Cachet Sellman
(74) *Attorney, Agent, or Firm* — LRK Patent LawFirm

(57) ABSTRACT

The present invention relates to a protein-binding material including a mesoporous silica and a method for selectively separating and purifying using the protein-binding material. More specifically, the present invention relates to a method of preparing a magnetic mesoporous silica responding to a magnetic field by adsorbing a precursor of a transition metal or its ion, such as an iron (Fe) precursor, onto a mesoporous silica, and to a protein-binding material prepared by coating the surface of the magnetic mesoporous silica with a transition metal or its ion so as to be capable of binding to a specific protein labeled with histidine, and also to a method of selectively separating and purifying a specific protein using the protein-binding material.

6 Claims, 7 Drawing Sheets

(56) References Cited

OTHER PUBLICATIONS

Kim et al. Magnetic Nanocomposite Spheres Decorated with NiO Nanoparticles for a Magnetically Recyclable Protein Separation System. Adv. Mater. 2010, 22, 57-60.*

T. Hyeon et al., "Nanocomposite Spheres Decorated with NiO Nanoparticles for a Magnetically Recyclable Protein Separation System", Advanced Materials, 2010. 22, 57-60, Wiley InterScience, Weinheim.

* cited by examiner

| Magnetic properties | HMMS$_{dm}$ | HMMS$_{co}$ | HMMS$_{coo}$ | HMMS$_{ro}$ | HMMS$_{oo}$ |
|---|---|---|---|---|---|
| Saturation magnetic flux density(emu/g) | 86.23 | 123.3 | 109.5 | 108.3 | 107.0 |
| Coercive force (emu) | 13.6 | 8.16 | 15.2 | 7.17 | 5.57 |

METHOD FOR PREPARING NI-CONTAINING MAGNETIC MESOPOROUS SILICA WHOSE SURFACE STRONGLY BINDS HISTIDINE-TAGGED PROTEIN, PROTEIN-BINDING MATERIAL FOR DEGRADING TOXIC AROMATIC COMPOUND COMPRISING THE MAGNETIC MESOPOROUS SILICA, AND METHOD FOR DEGRADING TOXIC AROMATIC COMPOUND USING THE MAGNETIC MESOPOROUS SILICA

CROSS REFERENCE TO RELATED APPLICATION

This application claims the benefit under 35 U.S.C. 119(a) of Korean Patent Application No. 10-2011-0035414, filed on Apr. 15, 2011, the disclosure of which is incorporated by reference in its entirety for all purposes.

This application incorporates by reference the sequence listing in a text file which is named P10407US.ST25, created on May 27, 2014, and 982 bytes in size.

BACKGROUND OF THE INVENTION

1. Field of the Invention

The present invention relates to a method for preparing an Ni-containing magnetic mesoporous silica whose surface strongly binds a histidine-tagged protein, a protein-binding material for degrading a toxic aromatic compound comprising the magnetic mesoporous silica, and a method for degrading a toxic aromatic compound using the magnetic mesoporous silica. More specifically, the present invention relates to a method of preparing a magnetic mesoporous silica responding to a magnetic field by adsorbing a precursor of a transition metal or its ion, such as an iron (Fe) precursor, onto a mesoporous silica, and to a protein-binding material prepared by coating the surface of the magnetic mesoporous silica with transition metal nickel (Ni) or its ion so as to be capable of binding to a specific protein such as histidine-tagged catechol dioxygenase enzyme, and also to a method of degrading a toxic aromatic compound using a histidine-tagged protein immobilized on the magnetic mesoporous silica.

2. Description of the Related Art

Magnetic nanoparticles have received increasing attention in various fields, including separation of biological or chemical substances, cell labeling and sorting, and magnetic resonance imaging, because they are convenient to use, can reduce processing time, and are easy to handle. The use of magnetic nanoparticles for the separation of DNAs and proteomes can reduce time and plays a very important role in increasing efficiency. However, it is not satisfactory for processing large amounts of samples or reducing time. It shows low efficiency because of the agglomeration and low surface reactivity of magnetic nanoparticles.

On the other hand, mesoporous silica materials have controllable pore sizes and large surface areas, and their surface is easy to functionalize. Due to these advantages, mesoporous silica materials have been used in various applications, including catalysts, nanomaterial supports, adsorption and separation processes, and sensors. In the process of preparing such mesoporous silica materials, iron oxide is allowed to react so as to impart magnetic properties to the mesoporous silica materials, such that the mesoporous silica materials can be easily separated from biological mixtures upon the application of an external magnetic field. Due to such properties, the magnetic mesoporous silica materials are expected to be useful for the separation and purification of biomolecules such as proteins or DNAs.

In the prior art, in order to impart magnetic properties to mesoporous silica materials, magnetic nanoparticles such as metals or iron oxides have been imbedded in mesoporous silica materials. However, in this method, magnetic nanoparticles are difficult to distribute uniformly in the aligned pores of mesoporous silica materials, and thus the magnetic nanoparticles clog the pores of the mesoporous silica materials, thereby reducing the surface area and magnetic susceptibility of the mesoporous silica materials. In an attempt to solve this problem, a method of applying magnetic nanoparticles to the wall portion of mesoporous silica materials was proposed, but the kind of magnetic nanoparticles applicable thereto is limited.

Other methods include a hard-templating method comprising depositing magnetic nanoparticles on templates and then removing the templates. The nano-casting method is applied in various ways to make metal oxides which are difficult to make by conventional methods. However, the metal oxides made according to this processing method have a low saturation magnetic field compared to pure metals.

The saturation magnetic field of a mesoporous silica material imparted with magnetic properties is determined by the amount and composition of the magnetic material. The composition of multi-component mesostructured alloys which were recently reported is easier to control than that provided by the hard-templating method. Many approaches have been proposed to develop magnetic mesoporous materials, but there still remain problems to be solved.

A method for the isolation and purification of a protein should have high selectivity for the protein and a minimal effect on the structure of the protein. Among protein purification methods, the use of a tag has good protein selectivity and a minimal effect on the protein structure. Various peptides and proteins are used as tags, and among them, a histidine tag is most frequently used. The histidine tag consists of 6 histidine residues. Thus, the histidine tag is advantageous in that it can purify a protein without influencing the original structure of the protein, because it is small in size. In addition to the histidine tag, a GST (Glutathione S-transferase)-tag is frequently used. The GST tag has protein selectivity much higher than the histidine tag, but it has a shortcoming in that it is large in size so that it should be cleaved after purification of the protein.

An existing method for the isolation and purification of a histidine-tagged protein is carried out using an IMAC column through the reversible binding between transition metal ions (such as $Co^{2+}$ or $Ni^{2+}$) and histidine. The IMAC column is prepared by coupling a chelating ligand to the column packing material and then coordinating transition metal ions. However, the packing materials that are used in this method have shortcomings in that the chelating ligand is prepared through a complex organic synthesis process and in that the separation and purification process is time-consuming.

It has long been known that histidine-tagged proteins easily bind to the surface of transition metal oxides. Recently, Professor Hyeon's Group (Seoul National University, Korea) reported the preparation of magnetic nanoparticles using iron oxide and nickel oxide and a technology of effectively separating a histidine-tagged protein using the magnetic nanoparticles (T. Hyeon et al., Nanocomposite Spheres Decorated with NiO Nanoparticles for a Magnetically Recyclable Protein Separation System. Adv. Mater. 2010, 22, 57-60).

As described above, the use of magnetic nanoparticles does not achieve satisfactory separation efficiency due to the agglomeration and low surface reactivity of the magnetic nanoparticles. Also, the existing mesoporous materials have low surface area and saturation magnetic field. In addition, the method of separating a protein using the IMAC column has problems in that a complex organic synthesis process should be carried out to synthesize the chelating ligand and in that a significant amount of time is required to isolate the protein, indicating that the IMAC column is difficult to use in a protein isolation process in which a reaction should be carried out within a short time.

SUMMARY OF THE INVENTION

Accordingly, the present invention has been made in view of the problems occurring in the prior art, and it is an object of the present invention to provide a method of: using a mesoporous silica material having large surface area to overcome the problem associated with the low surface area of magnetic nanoparticles; imparting magnetic properties to a mesoporous silica material using a precursor of a transition metal or its ionic by reduction with hydrogen so that the magnetic material is distributed uniformly in the mesoporous silica material at high density, whereby the mesoporous silica material can be easily handled using a magnetic field; and coating a mesoporous silica material with transition metal particles that bind selectively to specific amino acids, so that a histidine-tagged protein is effectively immobilized on the mosoporous silica material within a short time.

Another object of the present invention is to provide a method which can remove toxicity from a phenolic aromatic compound by breaking the structure of the phenolic aromatic compound using the magnetic mesoporous silica material immobilized with the histidine-tagged protein.

To achieve the above objects, the present invention provides a method for preparing a magnetic mesoporous silica whose surface strongly binds a histidine-tagged protein, the method comprising the steps of:

preparing a mesoporous silica, adding the mesoporous silica to an aqueous solution of a precursor, and uniformly stirring the resulting mesoporous silica-containing solution at room temperature for 2-3 hours to load the precursor onto the silica, thus obtaining a precursor-loaded silica;

filtering the precursor-loaded silica, freezing the filtered silica at a temperature between −70° C. and −80° C. for 1-2 hours, and then vacuum-drying the frozen silica at room temperature for 12-15 hours;

reducing the vacuum-dried silica in a hydrogen atmosphere at a temperature of 400~800° C. for 2-3 hours, thus obtaining a magnetic mesoporous silica having a plurality of pores formed therein;

adding the magnetic mesoporous silica to a transition metal aqueous solution containing a transition metal or its ions, ultrasonically treating the resulting magnetic mesoporous silica-containing solution at room temperature for 30-60 minutes, and stirring the ultrasonically treated solution at room temperature for 60-90 minutes;

filtering the stirred solution, freezing the filtered material at a temperature between −70° C. and −80° C. for 60-90 minutes, and then vacuum-drying the frozen material at room temperature for 12-15 hours; and reducing the vacuum-dried material in a hydrogen atmosphere at a temperature of 400~500° C. for 1-2 hours to adsorb and coat the transition metal or its ions onto the pores.

In the present invention, the pores preferably have a size of 7-10 nm.

In the present invention, the precursor is preferably a first-period transition metal or its ion which imparts magnetic properties.

In the present invention, the first-period transition metal or its ion is preferably a transition metal or its ion selected from the group consisting of iron, manganese, chromium, nickel, cobalt and zinc.

In the present invention, the transition metal or its ion which is adsorbed and coated onto the pores and surface of the magnetic mesoporous silica which strongly binds to the histidine-tagged protein is a transition metal or its ion selected from the group consisting of nickel, cobalt and zinc.

In the present invention, the histidine-tagged protein is preferably a protein comprising an amino acid selected from the group consisting of asparagine, arginine, cysteine, glutamine, lysine, methionine, proline and tryptophane.

In another aspect, the present invention provides a histidine-tagged protein-bound protein-binding material prepared by the steps of: adding the magnetic mesoporous silica, prepared by the above-described method, to a phosphate-buffered saline containing a histidine-tagged protein dissolved therein, to form a silica/protein-containing solution; stirring the silica/protein-containing solution at a temperature of 4~5° C. for 40-80 minutes to induce binding of the protein to the silica; separating the protein-bound silica from the solution using a magnet; and washing the separated silica with phosphate-buffered saline.

In the present invention, the histidine-tagged protein is preferably a protein comprising an amino acid selected from the group consisting of asparagine, arginine, cysteine, glutamine, lysine, methionine, praline and tryptophane.

In still another aspect, the present invention provides a method of degrading a toxic aromatic compound using a protein-binding material comprising a magnetic mesoporous silica, the method comprising the steps of:

preparing a biological mixture comprising a specific amino acid-containing protein tagged with histidine;

adding said protein-binding material to the biological mixture so that the protein-binding material selectively binds a specific protein contained in the biological mixture;

separating and capturing the specific protein-bound protein-binding material from the biological mixture by application of an external magnetic field; and separating and removing the captured protein-binding material from the biological mixture.

In still another aspect, the present invention provides a method of degrading a toxic aromatic compound using a protein-binding material comprising a magnetic mesoporous silica, the method comprising the steps of:

preparing a biological mixture comprising a specific amino acid-containing protein tagged with histidine;

adding said protein-binding material to the biological mixture so that the protein-binding material selectively binds the specific protein contained in the biological mixture;

separating and capturing the specific protein-bound protein-binding material from the biological mixture by application of an external magnetic field;

separating and removing the captured protein-binding material from the biological mixture; and purifying the bound specific protein from the separated protein-binding material.

BRIEF DESCRIPTION OF THE DRAWINGS

The above and other objects, features and advantages of the present invention will be more clearly understood from the following detailed description taken in conjunction with the accompanying drawing, in which.

DETAILED DESCRIPTION OF THE INVENTION

Figure 1:
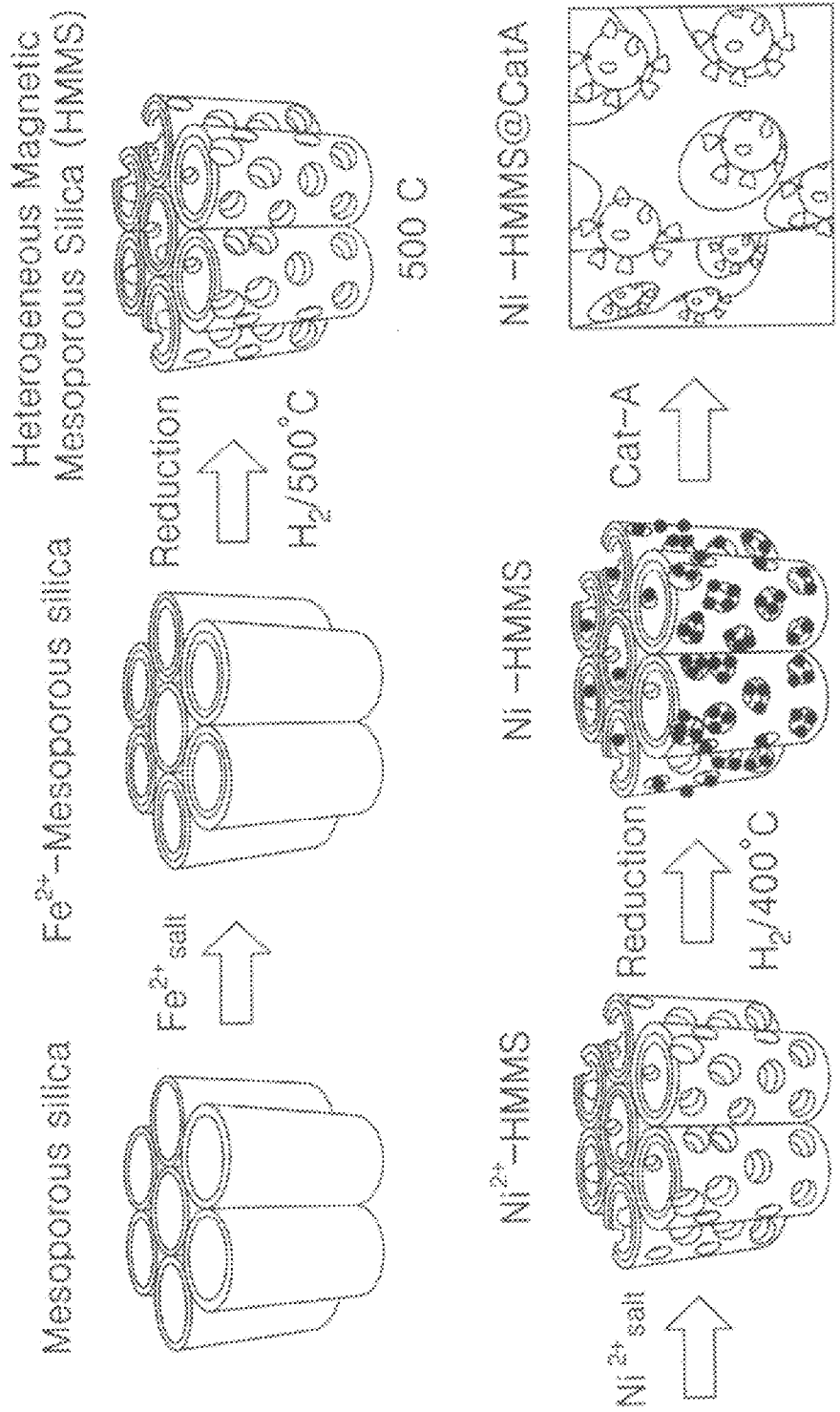
FIG. 1 is a schematic process view showing a process of preparing a nickel-coated magnetic mesoporous silica by making a magnetic mesoporous silica from a mesoporous silica and an iron precursor and binding nickel ions to the magnetic mesoporous silica and a process of immobilizing a histidine-tagged protein onto the nickel-coated magnetic mesoporous silica.

The present invention relates to a method of preparing a protein-binding material, which binds selectively a histidine-tagged protein to be separated, using a magnetic mesoporous silica, and a method of degrading a toxic phenolic aromatic compound using a protein immobilized on the magnetic mesoporous silica.

The inventive method for preparing a magnetic mesoporous silica whose surface strongly binds a histidine-tagged protein comprises the steps of: preparing a mesoporous silica, adding the mesoporous silica to an aqueous solution of a precursor, and uniformly stirring the resulting solution for 1-2 hours so as to load the precursor onto the silica, thereby obtaining a precursor-loaded silica (in this step, because long-time stirring in air can) cause oxidation, a suitable stirring time is required. Thus, the stirring is carried out for about 1-2 hours); filtering the precursor-loaded silica, freezing the filtered silica at a temperature between −70° C. and −80° C. for 1-2 hours, and then vacuum-drying the filtered silica at room temperature for 12-15 hours (in this step, in order to prevent Fe ions from being oxidized in air after impregnation thereof, the step of freezing the silica at a temperature below zero and drying the silica is carried out); reducing the vacuum-dried silica in a hydrogen atmosphere at a temperature of 400~800° C. for 2-3 hours to obtain a magnetic mesoporous silica having a plurality of pores formed therein (in this step, the reducing step consists of a heating time of 2 hours and a maintenance time of 2 hours, and the above-described reducing time range of 2-3 hours is determined considering only the maintenance time); adding the magnetic mesoporous silica to a transition metal aqueous solution containing a transition metal or its ions, ultrasonically treating the resulting mixture for 30-60 minutes, and then stirring the ultrasonically treated mixture for 60-90 minutes (in this step, the ultrasonic treatment is performed to effectively impregnate Ni ions, for example, into the silica, and the ultrasonic treatment time is preferably 30-60 minutes. Also, a suitable stirring time is required to prevent oxidation during stirring); filtering the stirred mixture, freezing the filtered material at a temperature between −70° C. and −80° C. for 60-90 minutes, and then vacuum-drying the frozen material at room temperature for 12-15 hours (in this step, in order to prevent Ni ions, for example, from being oxidized in air after impregnation thereof, the step of freezing the filtered material at a temperature below zero and drying the frozen material is carried out); and reducing the vacuum-dried material in a hydrogen atmosphere at a temperature of 400~800° C. for 1-2 hours to adsorb and coat the transition metal onto the pores (in this step, at 400~500° C. or higher, Ni particles, for example, are formed, and the aggregation of the formed particles increases so that the desired Ni particle size is not achieved. For this reason, the reducing temperature is set at 400~500° C. and more preferably 400° C. and the reduction reaction time consists of a heating time of 30 minutes and a maintenance time of 30 minutes. The reduction reaction was carried out while changing the heating time and/or the maintenance time, and as a result, the following optimal conditions were determined: a reducing time of 400° C.; a heating time of 30 minutes; and a maintenance time of 30 minutes).

In the present invention, the pores preferably have a size of 7-10 nm.

In the present invention, the precursor is preferably a first-period transition metal or its ion.

In the present invention, the first-period transition metal or its ion is a transition metal or its ion selected from the group consisting of iron, manganese, chromium, nickel, cobalt and zinc.

In the present invention, the transition metal or its ion which is adsorbed and coated onto the pores and surface of the magnetic mesoporous silica which strongly binds the histidine-tagged protein is a transition metal or its ion selected from the group consisting of nickel, cobalt and zinc.

In the present invention, the histidine-tagged protein is preferably a protein comprising an amino acid selected from the group consisting of asparagine, arginine, cysteine, glutamine, lysine, methionine, proline and tryptophane.

Also, the present invention provides a histidine-tagged protein-bound protein-binding material prepared by the steps of: adding the magnetic mesoporous silica, prepared by the above-described method, to a phosphate-buffered saline containing a histidine-tagged protein dissolved therein, to form a silica/protein-containing solution; stirring the silica/protein-containing solution at a temperature of 4~5° C. for 40-80 minutes to induce binding of the protein to the silica; separating the protein-bound silica from the solution using a magnet; and washing the separated silica with phosphate-buffered saline.

In the present invention, the histidine-tagged protein is preferably a protein comprising an amino acid selected from the group consisting of asparagine, arginine, cysteine, glutamine, lysine, methionine, proline and tryptophane.

Also, the present invention provides a method of degrading a toxic aromatic compound using a protein-binding material comprising a magnetic mesoporous silica, the method comprising the steps of: preparing a biological mixture containing a specific amino acid-containing protein labeled with histidine; adding said protein-binding material to the biological mixture so that the protein-binding material selectively binds the specific protein contained in the biological mixture; separating and capturing the specific protein-bound protein-binding material from the biological mixture by application of an external magnetic field; and separating and removing the captured protein-binding material from the biological mixture.

Also, the present invention provides a method of degrading a toxic aromatic compound using a protein-binding material comprising a magnetic mesoporous silica, the method comprising the steps of: preparing a biological mixture containing a specific amino acid-containing protein tagged with histidine; adding said protein-binding material to the biological mixture so that the protein-binding material selectively binds the specific protein contained in the biological mixture; separating and capturing the specific protein-bound protein-binding material from the biological mixture by application of an external magnetic field; separating and removing the captured protein-binding material from the biological mixture; and purifying the bound specific protein from the separated protein-binding material.

The protein-binding material according to the present invention comprises a magnetic mesoporous silica and is prepared by preparing a mesoporus silica, adsorbing a transition metal precursor onto the silica to prepare a magnetic mesoporous silica, and coating the surface of the magnetic mesoporous silica with a transition metal or its ion having the property of binding to a specific amino acid-containing protein tagged with histidine.

In the present invention, the transition metal or it ion is preferably a first-period transition metal or its ion, and more preferably a transition metal or its ion selected from the group consisting of iron, manganese, chromium, nickel, cobalt and zinc.

In the present invention, the specific protein is a protein comprising an amino acid selected from the group consisting of asparagine, arginine, cysteine, glutamine, lysine, methionine, proline and tryptophane, but is not limited thereto.

The present invention discloses a method of separating a specific amino acid-containing protein using the protein-binding material, the method comprising the steps of: preparing a biological mixture comprising a specific amino acid-containing protein tagged with histidine; adding to the biological protein a protein-binding material comprising a magnetic mesoporous silica coated with a transition metal or its ion, so that the protein-binding material selectively binds the specific protein contained in the biological mixture; separating and capturing the specific protein-bound protein-binding material from the biological mixture by application of an external magnetic field; and separating and removing the captured protein-binding material from the biological mixture.

Also, the present invention discloses a method of breaking the structure of a toxic aromatic compound, the method comprising the steps of: preparing a biological mixture comprising a specific amino acid-containing protein tagged with histidine; adding to the biological protein a protein-binding material comprising a magnetic mesoporous silica coated with a transition metal or its ion, so that the protein-binding material selectively binds the specific protein contained in the biological mixture; separating and capturing the specific protein-bound protein-binding material from the biological mixture by application of an external magnetic field; separating and removing the captured protein-binding material from the biological mixture; and breaking the ring structure of a phenolic aromatic compound using the specific protein immobilized on the separated protein-binding material, thus removing toxicity from the phenolic aromatic compound.

According to the present invention, the binding between the specific protein and the magnetic mesoporous silica is achieved by a reversible coordinate bond between the imidazole group of the histidine and the transition metal or transition metal ion present in the pores or on the surface of the magnetic mesoprous silica.

The mesoporous silica that is used in the present invention is note specifically limited, but is a silica prepared from a poly(alkylene oxide) block copolymer (e.g., Pluronic P123 (BASF) and tetraorthoethyl silicate (TEOS) as a silica source by a sol-gel reaction.

The mesoporous silica that is used in the present invention preferably has a pore size of 7-10 nm, and more preferably 8-9 nm.

The protein-binding material according to the present invention is prepared by impregnating the mesoporous silica with a first-period transition metal or its ion such as iron, manganese, chromium, nickel, cobalt or zinc to impart magnetic properties to the mesoporous silica and coating the surface of the mesoporous silica with an oxide of the selected transition metal or a transition metal ion.

Preferably, the protein which can reversibly bind to the magnetic mesoporous silica containing the transition metal or transition metal ion is a protein containing 4 to 12 consecutive histidine residues at the terminal region of the amino acid sequence thereof.

Hereinafter, the protein-binding material and the method for separating and purifying a protein using the same will ne described in further detail with reference to experimental examples. However, the scope of the present invention is not limited to these experimental examples.

In the experimental examples of the present invention, an iron (Fe) precursor was used as a transition metal precursor, and transition metal nickel was used as a coating material.

The experimental examples of the present invention describe a protein-binding material comprising a magnetic mesoporous silica coated with a transition metal or transition metal ion having the property of binding selectively to a specific amino acid-containing protein.

Example 1

Synthesis of Nickel Particle-Coated Magnetic Mesoporous Silica (Ni-HMMS)

In one embodiment of the present invention, a uniform nanoporous silica can be prepared from a mixed solution of Pluronic P123, HCl and double distilled water. The mixed solution becomes gradually transparent while being stirred. Specifically, the mixed solution was stirred in a water bath at 40° C. for 24 hours, after which tetraethyl orthosilicate (TEOS) was added thereto, and the mixture was stirred for 8 hours. The stirred solution was placed in a steel press and aged in a high-temperature oven for 8 hours. The aged solution was cooled to room temperature, washed with water, filtered, and dried at room temperature, thus obtaining powder. The dried powder was calcined at 550° C. for 6 hours, thus preparing a uniform mesoporous silica. The uniform mesoporous silica can be allowed to react with a compound capable of providing an iron (Fe) precursor, thus preparing a magnetic mesoporous silica (MS).

Figures 2, 3:
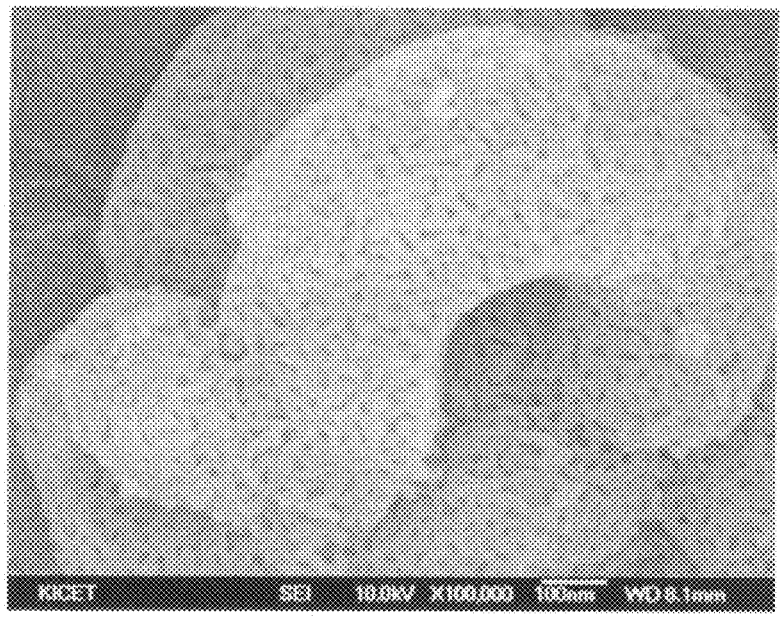
FIG. 2 is a scanning electron micrograph of a magnetic mesoporous silica prepared according to one embodiment of the present invention.
FIG. 3 shows the results of SQUID (superconducting quantum interference device) measurement of magnetic mesoporous silica materials prepared according to one embodiment of the present invention.
Figure 4:
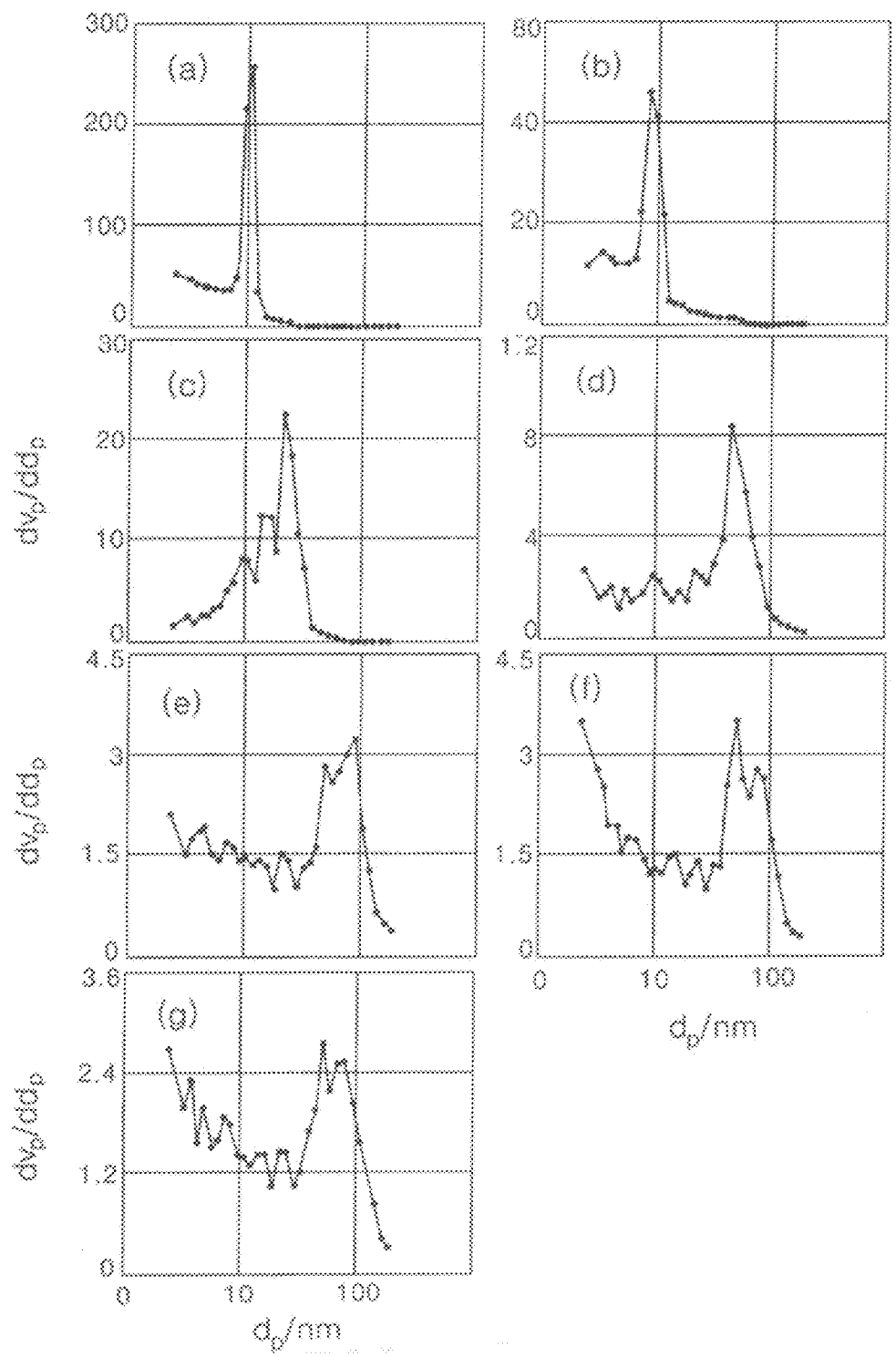
FIG. 4 shows nitrogen adsorption-desorption isotherms by the BJH (Barrett-Joyner-Halenda) method, measured for magnetic mesoporous silica materials prepared according to one embodiment of the present invention.

$FeCl_2.4H_2O$ (iron (II) chloride tetrahydrate) was dissolved in distilled water to prepare 250 ml of a 3M iron precursor aqueous solution. Then, 5 g of the uniform mesoporous silica powder was added to the iron precursor aqueous solution, and the mixture was stirred for 2 hours, whereby the iron precursor was loaded onto the mesoporous silica. The precursor-loaded silica was stored at −70° C. for 1 hour, and then dried in a vacuum at room temperature for 12 hours. The dried silica was reduced for 2 hours at each of 400, 500, 600, 700 and 800° C., thus preparing magnetic mesoporous silica materials (named $HMMS_{400}$, $HMMS_{500}$, $HMMS_{600}$, HMMS700, $HMMS_{800}$, respectively). HMMSs which were prepared at a temperature lower than 400° C. were easily oxidized and were not perfectly reduced, and thus they were not suitable for this experiment. Also, samples which were prepared at a temperature higher than 800° C. were excluded from this experiment, because the properties thereof did not greatly differ from those of the sample prepared at 800° C., even though they were not easily oxidized in air. Among the prepared samples, $HMMS_{500}$ prepared at a reducing temperature of 500° C. showed the highest saturation magnetic field and had a main pore size of 43.5 nm as can be seen in the BJH plot, and thus this material ($HMMS_{500}$) was selected as a material to be introduced with a functional group. A scanning electron micrograph of the prepared mesoporous silica material is shown in FIG. 2. Also, the SQUID measurement results and BJH (Barrett-Joyner-Halenda) plots of (a) MS, (b) Fe2+-MS, (c) $HMMS_{400}$, (d) $HMMS_{500}$, (e) $HMMS_{600}$, (f) $HMMS^{700}$, (g) $HMMS_{800}$ are shown in FIGS. 3 and 4, respectively.

Figure 5:
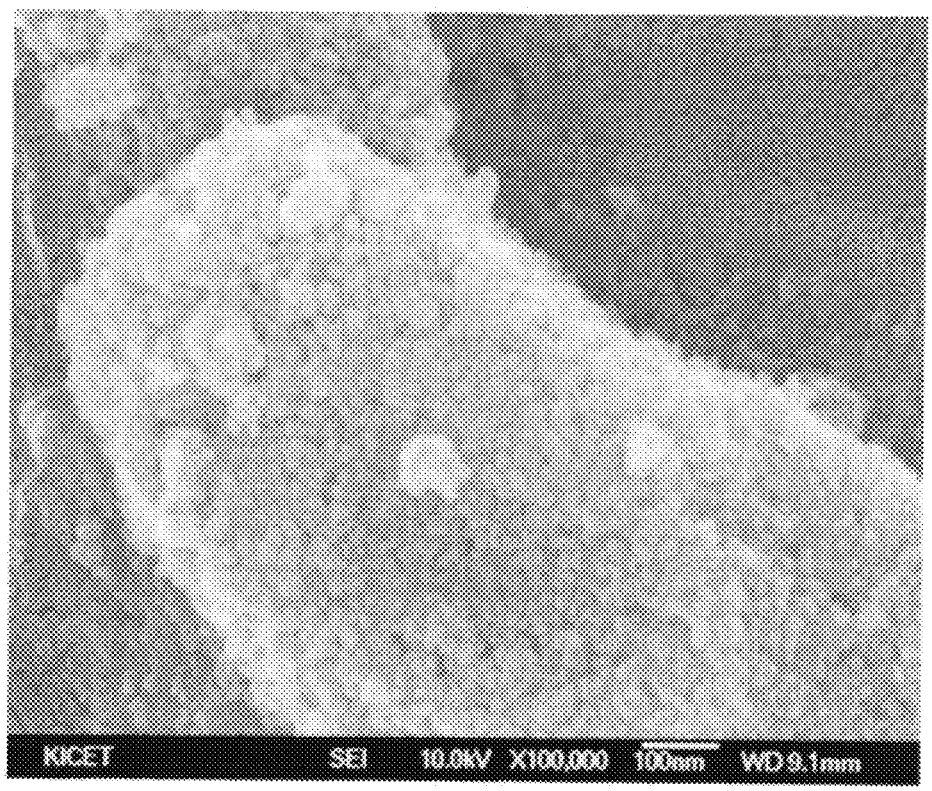
FIG. 5 is a scanning electron micrograph of a nickel particle-coated magnetic mesoporous silica (Ni-HMMS$_{500}$) prepared according to one embodiment of the present invention.
Figure 6:
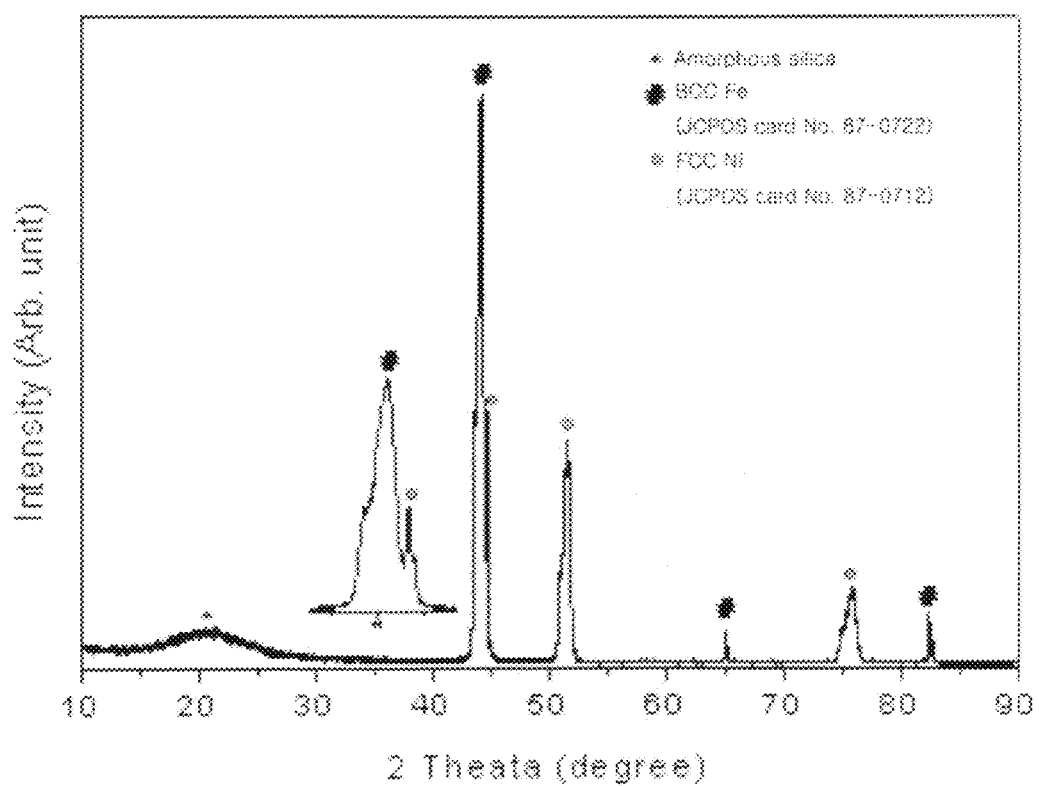
FIG. 6 is a graph showing the results of XRD analysis of nickel particles coated on the surface of a magnetic mesoporous silica prepared according to one embodiment of the present invention.

1 g of the prepared magnetic mesoporous silica material (HMMS500) was added to 10 ml of 1M $NiCl_2.6H_2O$ solution, and the mixture was ultrasonically treated at room temperature for 30 minutes and stirred for 1 hour. The stirred mixture was filtered, stored at −70° C. for 1 hour, and then dried in a vacuum at room temperature for 12 hours. The dried material was reduced in a hydrogen atmosphere at a temperature of 400–500° C. for 1-2 hours, thereby preparing a nickel particle-coated magnetic mesoporous silica material (Ni-$HMMS_{500}$). A scanning electron micrograph of the prepared nickel particle-coated magnetic mesoporous silica material is shown in FIG. 5. The nickel particles coated on the surface of the magnetic mesoporous silica material was identified as FCC Ni (JCPDS card (No. 87-0712)) by XRD analysis (FIG. 6).

Example 2

High-Level Expression of Catechol Dioxygenase

In order to obtain an enzyme to be immobilized on the magnetic mesoporous silica: genomic DNA was extracted from *Corynebacterium glutamicum* ATCC 13032, and catA3 gene was amplified by polymerase chain reaction (hereinafter referred to as "PCR") using the genomic DNA as a template with primers having nucleotide sequences of SEQ ID NOS: 1 and 2. The PCR amplification product was separated and purified by agarose gel electrophoresis. Each of the PCR-amplified catA3 gene and a pET-21a vector (Novegen, Madison, Wis., USA) was treated with NdeI, NotI and HindIII restriction enzymes and ligated with each other by $T_4$ DNA ligase to prepare a recombinant DNA vector, named "pSY-Cat". Then, the recombinant vector was transformed into *Escherichia coli* BL21 (Novagen, Madison, Wis., USA). Table 1 below shows the base sequences having the nucleotide primers of SEQ ID NOS: 1 and 2 used in the present invention.

TABLE 1

| SEQ ID NO | Number of bases | Remarks | Base sequence (5→3) |
|---|---|---|---|
| 1 | 27 | catA3-P3 (forward) | cagcatatgacaaccaccaccgcagac(NdeI) |
| 2 | 27 | catA3-P4 (reverse) | aataagcttcgcgcccggcgcgagcac(HindIII) |

The *E. coli* cells transformed with the pSY-Cat vector were cultured to the early exponential phase in a liquid medium (Luria-Bertani; hereinafter referred to as "LB"; 10 g/l Bactotryptone, 5 g/l Bacto yeast extract, 5 g/l NaCl) supplemented with 100 μg/ml of ampicillin, after which 0.5 mM IPTG (isopropyl β-D-1-thiogalactopyranoside) was added thereto to induce the over-expression the catA3 protein. Then, the cells were lysed and purified by affinity chromatography using His-tag.

Example 3

Figure 7:
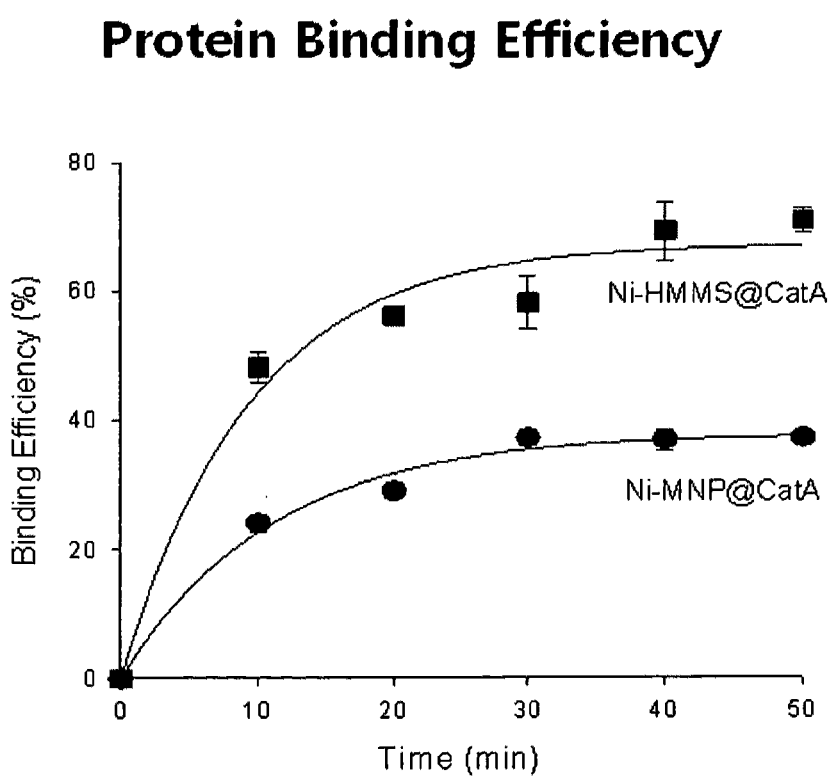
FIG. 7 shows a comparison of protein binding efficiency as a function of time between a nickel-coated magnetic mesoporous silica (Ni-HMMS) prepared according to one embodiment of the present invention and nickel/silica-magnetic nanoparticles (Ni/Si—Fe$_3$O$_4$) as a contol.

Binding of Enzyme to Nickel Particle-Coated Magnetic Mesoporous Silica 5 mg of the nickel particle-coated magnetic mesoporous silica (Ni-$HMMS_{500}$) prepared in Example 1 was added to a solution of histidine-tagged catechol dioxygenase enzyme (1 mg/ml) in 10 mM phosphate buffered saline (pH 7.4), and then stirred at 4° C. for about 1 hour. The enzyme-bound magnetic nanoparticles were separated from the solution using a magnet and washed twice with phosphate buffered saline. In the present invention, the enzyme-immobilized magnetic mesoporous silica prepared as described above was named "Ni-HMMS@CatA". For comparison, nickel nitrate was allowed to react with the surface of silica-magnetic nanoparticles) to prepare divalent nickel ion ($Ni^{2+}$)-bound silica-magnetic nanoparticles (Ni-MNPs) which were then immobilized with the enzyme in the same manner as above, thus preparing (Ni-MNPs@CatA). The amount of the enzyme immobilized on each of the nickel particle-coated magnetic mesoporous silica materials (Ni-HMMS@CatA and Ni-MNPs@CatA) was quantitatively analyzed by a BCA (bicinchoninic acid) test, thereby measuring the enzyme immobilization efficiency of each material FIG. 7 shows the enzyme immobilization efficiency of each material as a function of time.

Example 4

Figure 8:
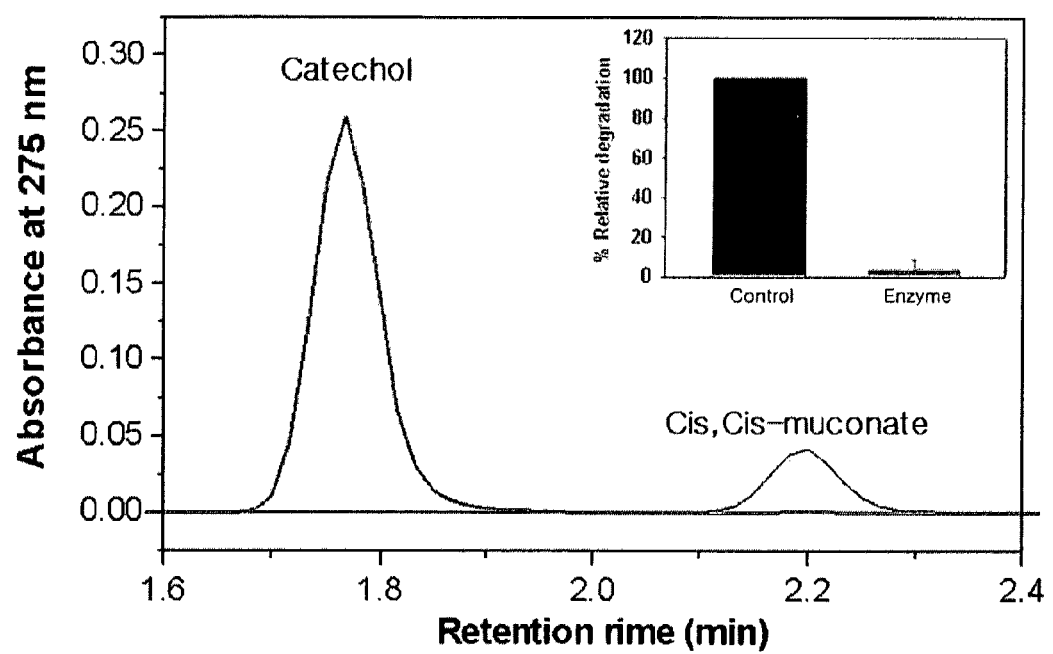
FIG. 8 shows the results of HPLC analysis for the efficiency of Ni-HMMS@CatA for the degradation of catechol which is a toxic aromatic compound.

Biogradation of Aromatic Compound by Enzyme Immobilized on Nickel Particle-Coated Magnetic Mesoporous Silica The enzyme-immobilized Ni-HMMS@CatA prepared as described above was used to degrade catechol, a poorly degradable compound. Specifically, 5 mg. of Ni-HMMS@CatA was added to 0.1 mM catechol solution and stirred at room temperature for 50 minutes. As a result, Ni-HMMS@CatA showed a degradation efficiency close to 100% (FIG. 8). Catechol was degraded into cis,cis-muconate. It could be seen that the catechol dioxygenase enzyme immobilized on the nickel particle-coated magnetic mesoporous silica effectively degraded catethol, a toxic aromatic compound.

As described above, the protein-binding material according to the present invention is prepared by impregnating a precursor of a transition metal or its ion into the mesoporous silica to impart magnetic properties to the mesoporous silica and coating the mesoporous silica with transition metal particles which bind to a specific protein tagged with histidine. Thus, the protein-binding material can easily bind to the histidine-tagged protein, and the histidine-tagged protein bound to the magnetic mesoporous silica can be effectively separated and purified from the biological mixture containing the histidine-tagged protein using an external magnetic field.

Also, according to the present invention, the magnetic mesoporous silica can be prepared such that the magnetic material is uniformly distributed at high density and has large surface area resulting in good reactivity, compared to existing methods. Moreover, the magnetic mesoporous silica is prepared using a cost-effective method without needing a complex separation process, unlike existing methods. The use of the magnetic mesoporous silica according to the present invention can easily separate and purify a specific protein within a short time and can achieve high separation and purification efficiency.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A method for preparing a magnetic mesoporous silica whose surface strongly binds a histidine-tagged protein, the method comprising the steps of:
   preparing a mesoporous silica, adding the mesoporous silica to an aqueous solution of a precursor, and stirring the resulting mesoporous silica-containing solution to load the precursor onto the mesoporous silica, thus obtaining a precursor-loaded mesoporous silica;
   filtering the precursor-loaded mesoporous silica, freezing the filtered precursor-loaded mesoporous silica at a temperature between −70° C. and -80° C., and then vacuum-drying the frozen precursor-loaded mesoporous silica at room temperature;
   reducing the vacuum-dried precursor-loaded mesoporous silica in a hydrogen atmosphere at a temperature of 400~800° C. for 2-3 hours, thus obtaining a magnetic mesoporous silica having a plurality of pores formed therein;
   adding the magnetic mesoporous silica to a transition metal aqueous solution containing a transition metal or an ion thereof, ultrasonically treating the resulting magnetic mesoporous silica-containing solution, and stirring the ultrasonically treated magnetic mesoporous silica containing solution;
   filtering the stirred magnetic mesoporous silica containing solution thereby obtaining a filtered material, freezing the filtered material at a temperature between −70° C. and −80° C., and then vacuum-drying the frozen material at room temperature; and

SEQUENCE LISTING

<160> NUMBER OF SEQ ID NOS: 2

<210> SEQ ID NO 1
<211> LENGTH: 27
<212> TYPE: DNA
<213> ORGANISM: Corynebacterium glutamicum
<220> FEATURE:
<221> NAME/KEY: misc_feature
<222> LOCATION: (1)..(27)
<223> OTHER INFORMATION: primer

<400> SEQUENCE: 1
cagcatatga caaccaccac cgcagac                                27

<210> SEQ ID NO 2
<211> LENGTH: 27
<212> TYPE: DNA
<213> ORGANISM: Corynebacterium glutamicum
<220> FEATURE:
<221> NAME/KEY: misc_feature
<222> LOCATION: (1)..(27)
<223> OTHER INFORMATION: primer

<400> SEQUENCE: 2
aataagcttc gcgcccggcg cgagcac                                27 reducing the vacuum-dried material in a hydrogen atmosphere at a temperature of 400~800° C. for 2-3 hours to adsorb and coat the transition metal or an ion thereof onto the pores of the magnetic mesoporous silica.

2. The method of claim 1, wherein the pores of the mesoporous silica have a size of 7-10 nm.

3. The method of claim 1, wherein the precursor is a first-period transition metal or an ion thereof which imparts magnetic properties.

4. The method of claim 3, wherein the first-period transition metal is selected from the group consisting of iron, manganese, chromium, nickel, cobalt and zinc.

5. The method of claim 1, wherein the transition metal or an ion thereof which is adsorbed and coated onto the pores and surface of the magnetic mesoporous silica is a transition metal or an ion thereof selected from the group consisting of nickel, cobalt and zinc.

6. The method of claim 5, wherein the histidine-tagged protein is a protein comprising an amino acid selected from the group consisting of asparagine, arginine, cysteine, glutamine, lysine, methionine, proline and tryptophane.

\* \* \* \* \*